United States Patent
Yang et al.

(10) Patent No.: US 11,247,198 B2
(45) Date of Patent: Feb. 15, 2022

(54) MOLECULAR SIEVE CATALYST, PREPARATION METHOD THEREFOR AND APPLICATION THEREOF

(71) Applicant: Dalian Institute of Chemical Physics, Chinese Academy of Sciences, Dalian (CN)

(72) Inventors: Miao Yang, Dalian (CN); Peng Tian, Dalian (CN); Zhongmin Liu, Dalian (CN); Bing Li, Dalian (CN); Lin Liu, Dalian (CN); Shiyun Sang, Dalian (CN)

(73) Assignee: Dalian Institute of Chemical Physics, Chinese Academy of Sciences, Dalian (CN)

(*) Notice: Subject to any disclaimer, the term of this patent is extended or adjusted under 35 U.S.C. 154(b) by 0 days.

(21) Appl. No.: 16/767,300

(22) PCT Filed: Dec. 20, 2017

(86) PCT No.: PCT/CN2017/117561
§ 371 (c)(1),
(2) Date: May 27, 2020

(87) PCT Pub. No.: WO2019/104778
PCT Pub. Date: Jun. 6, 2019

(65) Prior Publication Data
US 2020/0406242 A1  Dec. 31, 2020

(30) Foreign Application Priority Data
Nov. 29, 2017 (CN) .......................... 201711232744.6

(51) Int. Cl.
| C07C 1/20 | (2006.01) |
|---|---|
| B01J 29/85 | (2006.01) |
| B01J 29/70 | (2006.01) |
| C07C 11/06 | (2006.01) |
| C07C 11/04 | (2006.01) |

(52) U.S. Cl.
CPC ........... B01J 29/85 (2013.01); B01J 29/7003 (2013.01); C07C 1/20 (2013.01); C07C 11/04 (2013.01); C07C 11/06 (2013.01); C07C 2529/06 (2013.01); C07C 2529/70 (2013.01); C07C 2529/85 (2013.01)

(58) Field of Classification Search
CPC ........... C07C 1/20; C07C 11/06; C07C 11/04; C07C 2529/70; C07C 2529/85; C07C 2529/84; C07C 2529/83; C07C 2529/06
USPC ........ 585/520, 530, 532, 533, 638, 639, 640
See application file for complete search history.

(56) References Cited

U.S. PATENT DOCUMENTS

| 4,752,651 A | 6/1988 | Kaiser |
|---|---|---|
| 5,191,141 A | 3/1993 | Barger et al. |
| 2004/0116757 A1 | 6/2004 | Van Egmond et al. |
| 2009/0234171 A1 | 9/2009 | Cao |
| 2014/0005457 A1* | 1/2014 | Spannhoff ................ B01J 29/40 585/467 |
| 2016/0310934 A1* | 10/2016 | Braunsmann ........ B01J 37/0236 |

FOREIGN PATENT DOCUMENTS

| CN | 102451749 A | 5/2012 |
|---|---|---|
| CN | 102557073 A | 7/2012 |
| CN | 103551188 A | 2/2014 |
| CN | 103663490 A | 3/2014 |
| CN | 106365992 A | 2/2017 |
| EA | 007979 B1 | 2/2007 |
| EA | 009856 B1 | 4/2008 |
| EP | 2517775 A2 | 10/2012 |
| EP | 2660203 A1 | 11/2013 |
| RU | 2127717 C1 | 3/1999 |
| RU | 2276668 C2 | 5/2006 |
| RU | 2357963 C2 | 6/2009 |
| RU | 2422418 C2 | 6/2011 |
| RU | 2487856 C2 | 7/2013 |
| WO | 02058820 A1 | 8/2002 |
| WO | 2016/094174 A1 | 6/2016 |

OTHER PUBLICATIONS

Wang, Yuli, Notification of the First Office Action—Application No. 201711232744.6, dated Mar. 20, 2020, State Intellectual Property Office of the People's Republic of China.
Wang, Yuli, Search Report—Application No. 201711232744.6, dated Mar. 15, 2020, State Intellectual Property Office of hte People's Republic of China.
Baerlocher et al., Atlas of Zeolite Framework Types, 2007, pp. 31, 51, 87, 97, 113, 121, 147, 263, 313, 331, and 355, Sixth Revised Edition, Elsevier.
Wang, Baoli, Notification of the Third Office Action—Application No. 201711232744.6, dated Oct. 20, 2020, State Intellectual Property Office of the People's Republic of China.
Wang, Baoli, Supplementary Search Report—Application No. 201711232744.6, dated Oct. 10, 2020, State Intellectual Property Office of the People's Republic of China.

(Continued)

*Primary Examiner* — Elizabeth D Wood
(74) *Attorney, Agent, or Firm* — Edwin A. Sisson, Attorney at Law, LLC; Jeffrey J. Banyas

(57) ABSTRACT

The present application discloses a catalyst, the catalyst contains a molecular sieve, there is at least one-dimension 8-membered ring channel in the molecular sieve structure, the diameter of a diffusible substance in the direction of the 8-membered ring channel is no less than 2.0 Å, the diameter of a substance that can be accommodated in the molecular sieve structure is no more than 6 Å; the catalyst is used for a methanol and/or dimethyl ether to propylene reaction, comprising contacting methanol and/or dimethyl ether with a methanol-to-propylene catalyst to obtain propylene.

8 Claims, 2 Drawing Sheets

(56) References Cited

OTHER PUBLICATIONS

Van Der Poel, Wim, "Supplementary EP-Search Report: EPO Application No. EP 17933212", dated Nov. 16, 2020.
Gomes Elisa S et al, Strategy to design zeolite catalysts in the presence of biomass, Microporous and Mesoporous Materials, Apr. 4, 2017, 28-36, vol. 254, Elsevier, Online.

* cited by examiner

MOLECULAR SIEVE CATALYST, PREPARATION METHOD THEREFOR AND APPLICATION THEREOF

PRIORITIES AND CROSS REFERENCES

This Application claims priority from Chinese Application No. 201711232744.6 filed on 29 Nov. 2017 and International Application No. PCT/CN2017/117561 filed on 20 Dec. 2017 the teachings of each of which are incorporated by reference herein in their entirety.

TECHNICAL FIELD

The present application relates to a molecular sieve catalyst, a preparation method and application thereof, which belongs to the field of chemical catalysts.

BACKGROUND

Propylene is an important chemical raw material, mainly used in the production of chemical products such as polypropylene (PP), propylene oxide (PO), acrylonitrile (AN), acrylic acid (AA), and terminal applications involving packaging, construction, automobile, spinning, and daily chemical industry and many other fields. At present, the global demand for propylene is increasing year by year, benefiting from China's economic development, China's propylene consumption is also growing rapidly.

At present, the methods for preparing propylene at home and abroad mostly use petroleum as raw materials, while China's petroleum resources are very scarce, and oil reserves and output cannot meet the needs of the rapid development of the national economy, and the contradiction between supply and demand is prominent. The technology of methanol/dimethyl ether-to-olefins (MTO) and methanol/dimethyl ether-to-propylene (MTP) from coal can make use of abundant coal and natural gas resources, and is an advantageous alternative and supplement for obtaining olefins from petroleum routes.

The key to MTP technology is the development of high performance catalysts. HZSM-5 molecular sieve is the first choice for MTP catalyst because of its suitable pore size and acid properties. In the 1990s, Lurgi company in German developed a MTP fixed bed process with high selectivity to propylene based on a modified high-silicon-aluminum ratio ZSM-5 molecular sieve. The process seeks to maximize the yield of propylene. In the process, ethylene and C4+ hydrocarbons are separated from propylene and recycled to the MTP reaction system, so that the conversion rate of raw material of methanol is greater than 99%, and the yield of propylene carbon-based is as high as 71%. In recent years, Sinopec and Tsinghua University have also developed S-MTO/MTP and FMTP technology.

The MTP catalysts currently used in the industry all use ZSM-5 as a molecular sieve catalyst. In addition, there are related reports of using SAPO-34 and SAPO-18 molecular sieves in MTP reaction. The selectivity to propylene based on these catalysts is limited, and improving the single-pass selectivity to propylene is the most important challenge in the current research on MTP reaction.

SUMMARY OF THE INVENTION

According to an aspect of the present invention, a catalyst comprising a molecular sieve is provided, there is at least one-dimensional 8-membered ring small hole channel in the molecular sieve structure, the diameter of a diffusible substance in the direction of the 8-membered ring channel is no less than 2.0 Å, the diameter of a substance that can be accommodated in the molecular sieve structure is no more than 6 Å;

The catalyst is used for the reaction of methanol and/or dimethyl ether to propylene.

Preferably, the molecular sieve structure contains one-dimensional, two-dimensional or three-dimensional 8-membered ring hole channels, and the diameter of the diffusible substance in the direction of channel is no less than 2.0 Å.

Preferably, the space structure can accommodate a substance with a diameter in a range of 4.8 Å to 6 Å.

Preferably, the skeleton type of the molecular sieve is at least one selected from AFN, DFT, PHI, SIV, THO, APD, CAS, EDI, GIS and VNI.

Preferably, the molecular sieve is at least one selected from silicoaluminophosphate molecular sieve, aluminosilicate molecular sieve, and transition metal-substituted aluminophosphate molecular sieve.

Preferably, the catalyst comprises a transition metal-substituted aluminophosphate molecular sieve, and the preparation method comprises:

Adding a transition metal raw material, an aluminum source, a phosphorus source, a templating agent and a solvent into a synthesis kettle, and the transition metal-substituted aluminophosphate molecular sieve is obtained after crystallization;

The solvent is water, organic amine or ionic liquid.

According to still another aspect of the present invention, a method for preparing propylene from methanol and/or dimethyl ether is provided, comprising bringing methanol and/or dimethyl ether into contact with a methanol to propylene catalyst to obtain propylene;

The methanol to propylene catalyst comprises the catalyst provided in the present application.

Preferably, the methanol to propylene catalyst contains at least one of aluminosilicate molecular sieve, silicoaluminophosphate molecular sieve and transition metal-substituted aluminophosphate molecular sieve;

The reaction temperature for bringing methanol and/or dimethyl ether into contact with the methanol to propylene catalyst is in a range of 300° C. to 500° C.

Preferably, the conversion rate of the raw material is greater than 75% in the method.

Preferably, the single pass selectivity to propylene is greater than 60% in the method.

The beneficial effects that can be produced by this application include:

1) The molecular sieve catalyst provided by the present application has a good catalytic effect on the MTP reaction, and the conversion rate of methanol may be up to more than 80% by using the catalyst provided by the invention, and the catalyst of the invention can solve the problem of poor MTP reaction selectivity in the prior art, with a single pass propylene selectivity higher than 60%;

2) The catalyst molecular sieve of the present invention has various compositions, as long as it can drive the MTP reaction, so that different molecular sieves can be selected according to actual needs.

DETAILED DESCRIPTION OF THE EMBODIMENT

Figure 1:
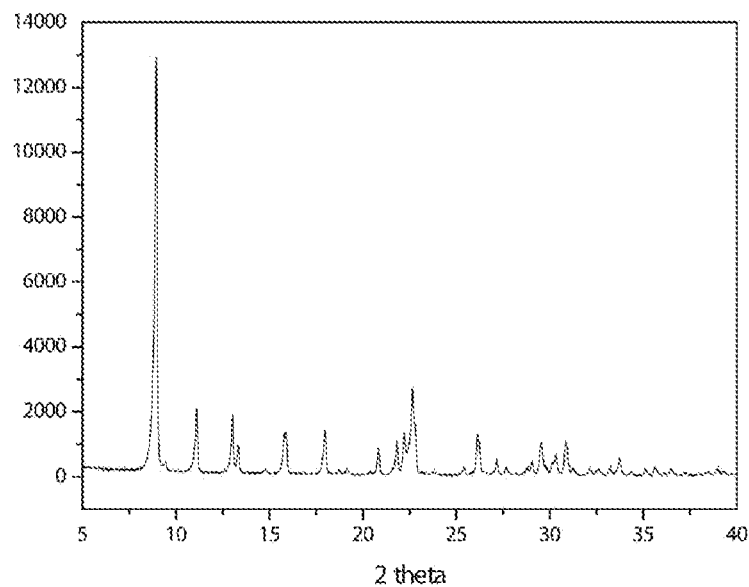
FIG. 1 is an XRD spectrum of the synthesized sample in Example 1.

The present invention will be further described below in conjunction with examples. It should be understood that these examples are only used to illustrate the present invention and not to limit the scope of the present invention. The experimental methods without specific conditions in the following examples generally follow the conventional conditions or the conditions recommended by the manufacturer. Without special instructions, the raw materials used in this application are purchased through commercial ways and used directly without special treatment.

The test conditions for this application are as follows:

The catalyst was tabletted and crushed to 20-40 mesh, and calcined at 600° C. for 4 hours by introducing air. 0.3 g of this sample was placed in a fixed bed reactor (home-made) as a catalyst for MTP reaction evaluation, and the reactor was a quartz tube. The reaction was carried out by activating for 1 hour with nitrogen introduced at 550° C. and then cooling to a target temperature. Methanol was carried by nitrogen. The reaction product was analyzed by on-line gas chromatography (Agilent A7890) on a PoraPlot-Q-HT column.

The elemental composition of the catalyst was measured using a Philips Magix 2424X type ray fluorescence analyzer (XRF).

X-ray powder diffraction phase analysis (XRD) of the catalyst was carried out using an X'Pert PRO X-ray diffractometer from PANalytical Company, the Netherlands with a Cu target, a Kα radiation source (λ=0.15418 nm), a voltage of 40 kV, and a current of 40 mA.

The specific surface area and pore size distribution of the samples were determined using an ASAP 2020 physical adsorption instrument from American Micromeritics Company. Before the analysis, the sample was preheated at 350° C. for 6 h, and the free volume of the sample tube was measured with He as the medium. When the sample was analyzed, the physical adsorption and desorption measurements were carried out at a liquid nitrogen temperature of 77 K using nitrogen as an adsorption gas. The specific surface area of the material was determined by the BET formula; the total pore volume of the material was calculated using the adsorption amount of N$_2$ at the relative pressure (P/P$_0$) of 0.99. The micropore surface area and pore volume of micropore were calculated by the t-plot method. When calculated, the cross-sectional area of the N$_2$ molecule is taken as 0.162 nm$^2$.

Temperature-programmed desorption of the sample after saturated adsorption of NH$_3$ was measured by an Autochem 2920 chemical adsorption instrument from American Micromeritics Company. The sample was activated for 60 min at 600° C. in He atmosphere of 40 mL/min. After the temperature was lowered to 100° C., ammonia gas was injected to saturate the sample, and the physically adsorbed NH$_3$ was removed by He purge, and then the temperature was programmed to 600° C. at a heating rate of 10° C./min, and the NH$_3$ desorption signal was recorded using a TCD monitor.

The present invention will be further described below in conjunction with examples.

Example 1

Synthesis of MnAPO-AFN Molecular Sieve

MnCl$_2$.4H$_2$O, deionized water, aluminum isopropoxide, oxalic acid, 1,3-propanediamine (1,3-PDA) and phosphoric acid (85%) were added to a 100 mL stainless steel reaction kettle at a time. The molar ratio of the reactants was MnCl$_2$.4H$_2$O:Al(iPrO)$_3$:H$_3$PO$_4$:H$_2$C$_2$O$_4$:1,3PDA:H$_2$O=(1.0:1.4:5.0:1.6:5.0:920). The raw material mixture was stirred uniformly, then sealed, and heated to 180° C. under stirring, and crystallized by rotation for 72 h. The solid product was separated by centrifugation, washed with deionized water to neutrality, and dried in air at 120° C. to obtain a molecular sieve sample S1 to be used, named MnAPO-AFN.

Example 2

Synthesis of SAPO-AFN Molecular Sieve

A certain amount of aluminum isopropoxide, deionized water, triethylenediamine (DABCO), tetraethyl orthosilicate, and phosphoric acid (85%) were sequentially added to a 100 mL synthesis kettle. The molar ratio of the reactants was Al$_2$O$_3$:P$_2$O$_5$:SiO$_2$:DABCO:H$_2$O=(1.0:1.0:0.3:3.0:50). The raw material mixture was stirred uniformly, then sealed, and heated to 200° C. under stirring, and crystallized by rotation for 40 h. The solid product was separated by centrifugation, washed with deionized water to neutrality, and dried in air at 120° C. to obtain a molecular sieve sample S2 to be used, named SAPO-AFN.

Example 3

Synthesis of CoAlPO-DFT Molecular Sieve 13.2 g of cobalt carbonate was dissolved in 108.23 g of deionized water and 26.78 g of phosphoric acid (85%). 10 g of aluminum isopropoxide, 10.32 g of phosphoric acid and 53 g of ethylene glycol were uniformly mixed in another beaker, and stirred at room temperature for 24 hours. 23.41 g of the ethylene glycol solution prepared above was mixed with an aqueous solution containing cobalt and uniformly stirred for 20 minutes, and then 30 g of the solution was taken out, and 1.05 g of quinine, 3.08 g of piperazine and 0.6 ml of ethylenediamine were added into the solution. The raw material mixture was stirred uniformly, then sealed, heated to 180° C. with stirring, and crystallized by rotation for 96 hours. The solid product was separated by centrifugation, washed with deionized water to neutrality, and dried in air at 100° C. to obtain a molecular sieve sample S3 to be used, named CoAlPO-DFT.

Example 4

Synthesis of SAPO-DFT Molecular Sieve

A certain amount of pseudoboehmite (65 wt %), deionized water, 1,3 propylenediamine (1,3-DPA), silica sol (31 wt %), and phosphoric acid (85%) were sequentially added to a 100 mL synthesis kettle. The molar ratio of the reactants was Al$_2$O$_3$:P$_2$O$_5$:SiO$_2$:1,3-DPA:H$_2$O=(1.0:1.0:0.3:5.0:50). The raw material mixture was stirred uniformly, then sealed, heated to 180° C. with stirring, and crystallized by rotation for a time in a range of 12 hours to 72 hours. The solid product was separated by centrifugation, washed with deionized water to neutrality, and dried in air at 120° C. to obtain a molecular sieve sample S4 to be used, named SAPO-DFT.

Example 5

Synthesis of ZnAlPO-PHI Molecular Sieve

Zinc oxide, aluminum hydroxide, deionized water, phosphoric acid, ethylene glycol (EG) and N,N-dimethyl-1,3-propanamine ($C_5H_{14}N_2$) were sequentially added to a 100 mL synthesis kettle. The molar ratio of the reactants was $ZnO:P_2O_5:Al_2O_3:C_5H_{14}N_2:20H_2O:100EG=(3:5:1:8:20:100)$. The raw material mixture was stirred uniformly, then sealed, heated to 180° C. with stirring, and crystallized by rotation for 48 hours. The solid product was separated by centrifugation, washed with deionized water to neutrality, and dried in air at 100° C. to obtain a molecular sieve sample S5 to be used, named ZnAlPO-PHI.

Example 6

Synthesis of SiAl-PHI Molecular Sieve

A certain amount of KOH, deionized water, sodium silicate solution ($Na_2O$: 8.9%, $SiO_2$: 28.7%) and sodium metaaluminate (30.5% $Na_2O$, 45.6% $Al_2O_3$) were sequentially added to a 100 mL synthesis kettle. The molar ratio of the reactants was $Na_2O:K_2O:Al_2O_3:SiO_2:H_2O=(6.95:3.5:1.0:22:350)$. The raw material mixture was stirred uniformly, then sealed, heated to 120° C. with stirring, and crystallized by rotation for 12 hours. The solid product was separated by centrifugation, washed with deionized water to neutrality, and dried in air at 100° C. to obtain a molecular sieve sample S6 to be used, named SiAl-PHI.

Example 7

Synthesis of CoAlPO-SIV Molecular Sieve

Phosphoric acid, aluminum isopropoxide, $Co(OH)_2$, ethylmethylimidazolium bromide ionic liquid (IL) and hydrofluoric acid were sequentially added to a 100 mL stainless steel synthesis kettle. The molar ratio of the reactants was $Al(iPrO)_3:H_3PO_4:HF:IL:Co(OH)_2:6H_2O=(1.0:2.9:0.69:40:1.6:3.6)$. The raw material mixture was stirred uniformly, then sealed, heated to 170° C. with stirring, and crystallized by rotation for 72 hours. The solid product was separated by centrifugation, washed with deionized water to neutrality, and dried in air at 100° C. to obtain a molecular sieve sample S7 to be used, named CoAlPO-SIV.

Example 8

Synthesis of SAPO-SIV Molecular Sieve

A certain amount of aluminum hydroxide, deionized water, isopropylamine (IPA), white carbon black, ethylmethylimidazolium bromide ionic liquid (IL), hydrofluoric acid and phosphoric acid (85%) were sequentially added to a 100 mL synthesis kettle. The molar ratio of the reactants was $Al_2O_3:1.0\ P_2O_5:0.3SiO_2:IL:0.3HF:IPA:H_2O=(1.0:1.0:0.3:25:0.3:2.0:10)$. The raw material mixture was stirred uniformly, then sealed, heated to 180° C. with stirring, and crystallized by rotation for 48 hours. The solid product was separated by centrifugation, washed with deionized water to neutrality, and dried in air at 120° C. to obtain a molecular sieve sample S8 to be used, named SAPO-SIV. The specific surface area and pore volume of the sample were measured after being calcined to remove the template. The sample had a high BET specific surface area of 412.8 $m^2\ g^{-1}$, and a large pore volume of 0.24 $cm^3\ g^{-1}$, wherein the specific surface area and pore volume of micropore calculated by the t-plot method were 360.5 $m^2\ g^{-1}$ and 0.18 $cm^3\ g^{-1}$ respectively.

Example 9

Synthesis of ZnAlPO-THO Molecular Sieve

Zinc oxide, aluminum isopropoxide, phosphoric acid, ethylene glycol (EG) and 1,3 propylenediamine (1,3-DPA) were sequentially added to a 100 mL synthesis kettle. The molar ratio of the reactants was $ZnO:P_2O_5:Al_2O_3:1, 3\text{-}DPA:EG=(3:5:1:8:120)$. The raw material mixture was stirred uniformly, then sealed, heated 180° C. with stirring, and crystallized by rotation for 96 hours. The solid product was separated by centrifugation, washed with deionized water to neutrality, and dried in air at 100° C. to obtain a molecular sieve sample S9 to be used, named ZnAlPO-THO.

Example 10

Synthesis of SAPO-THO Molecular Sieve

Pseudoboehmite, deionized water, piperidine ($C_5H_{11}N$), white carbon black and phosphoric acid (85%) were sequentially added to a 100 mL synthesis kettle. The molar ratio of the reactants was $1.0\ Al_2O_3:1.0\ P_2O_5:0.3\ SiO_2:3.0\ C_5H_{11}N:40\ H_2O=(1:1:0.3:3.0:40)$. The raw material mixture was stirred uniformly, then sealed, heated 180° C. with stirring, and crystallized by rotation for a time in a range of 12 hours to 72 hours. The solid product was separated by centrifugation, washed with deionized water to neutrality, and dried in air at 120° C. to obtain a molecular sieve sample S10 to be used, named SAPO-THO.

Example 11

Synthesis of SAPO-APD Molecular Sieve

Aluminum isopropoxide, deionized water, ethanolamine (ETA), silica sol (30%), and phosphoric acid (85%) were sequentially added to a 100 mL synthesis kettle. The molar ratio of the reactants was $Al_2O_3:P_2O_5:SiO_2:ETA:H_2O=(1:1.4:0.3:7:140)$. The raw material mixture was stirred uniformly, then sealed, heated 160° C. with stirring, and crystallized by rotation for 72 hours. The solid product was separated by centrifugation, washed with deionized water to neutrality, and dried in air at 120° C. to obtain a molecular sieve sample S11 to be used, named SAPO-APD. The surface acidity of the molecular sieve was studied by $NH_3$-TPD method. The $NH_3$-TPD curve is shown in FIG. 1. The sample shows a very high desorption peak around 170° C. and only a short, wide envelope peak at 370° C., which shows that the sample is very weak in acidity.

Example 12

Synthesis of SiAl-CAS Molecular Sieve

Piperazine, deionized water, LudoxAS-40, sodium aluminate and HF were sequentially added to a synthesis kettle.

The molar ratio of the reaction mixture was $Na_2O:Al_2O_3$:$SiO_2:C_4H_{10}N_2:HF:H_2O$=(1:1:10:5.6:77). The reaction mixture was stirred uniformly, then sealed, heated 150° C. with stirring, and crystallized by rotation for 48 hours. The solid product was separated by centrifugation, washed with deionized water to neutrality, and dried in air at 100° C. to obtain a molecular sieve precursor 1. The precursor 1 was placed in a tube furnace and heated up to 1000° C. at a heating rate of 1 degree/minute, and heated for 10 hours to obtain a target product of molecular sieve S12, named SiAl-CAS.

Example 13

Synthesis of SAPO-CAS Molecular Sieve

Pseudoboehmite, deionized water, piperazine (PIP), silica sol (30%) and phosphoric acid (85%) were sequentially added to a 100 mL synthesis kettle. The molar ratio of the reactant was $Al_2O_3:P_2O_5:SiO_2:PIP:H_2O$=(1:1:0.3:3:40). The reaction mixture was stirred uniformly, then sealed, heated 160° C. with stirring, and crystallized by rotation for 12 hours. The solid product was separated by centrifugation, washed with deionized water to neutrality, and dried in air at 120° C. to obtain a molecular sieve sample S13 to be used, named SAPO-CAS.

Example 14

Synthesis of CoAlPO-EDI Molecular Sieve 12.8 g of cobalt nitrate, 23.2 g of aluminum nitrate, 27.16 phosphoric acid (2 M), 8.9 g of 1,2-propylenediamine, and 100 g of deionized water were sequentially added to a 200 mL synthesis kettle. The raw material mixture was stirred uniformly, then sealed, heated to 150° C. with stirring, and crystallized by rotation for 48 hours. The solid product was separated by centrifugation, washed with deionized water to neutrality, and dried in air at 100° C. to obtain a molecular sieve sample S14 to be used, named CoAlPO-EDI.

Example 15

Synthesis of SiAl-EDI Molecular Sieve

A certain amount of KOH, deionized water, aluminum powder, and white carbon black were sequentially added to a 100 mL synthesis kettle. The molar ratio of the reactant was $K_2O:Al_2O_3:SiO_2:H_2O$=(5:1:3:100). The raw material mixture was stirred uniformly, then sealed, heated 100° C. with stirring, and crystallized by rotation for 96 hours. The solid product was separated by centrifugation, washed with deionized water to neutrality, and dried in air at 100° C. to obtain a molecular sieve sample S15 to be used, named SiAl-EDI.

Example 16

Synthesis of SAPO-EDI Molecular Sieve

Pseudoboehmite, deionized water, trimethylamine (TMA), tetraethylammonium hydroxide (35%), silica sol (30%), and phosphoric acid (85%) were sequentially added to a 100 mL synthetic kettle. The molar ratio of the reactant was $Al_2O_3:P_2O_5:SiO_2:TEA_2O:TMA:H_2O$=(1:1:0.3:1.5:2:40). The raw material mixture was stirred uniformly, then sealed, heated 170° C. with stirring, and crystallized by rotation for a time in a range of 12 hours to 72 hours. The solid product was separated by centrifugation, washed with deionized water to neutrality, and dried in air at 120° C. to obtain a molecular sieve sample S16 to be used, named SAPO-EDI.

Example 17

Synthesis of SiAl-GIS Molecular Sieves

A certain amount of sodium fluoride, deionized water and kaolin ($Al_2O_3:SiO_2:H_2O$=1:2:2.2) were sequentially added to a 100 mL synthetic kettle. The molar ratio of the reactant was $Al_2O_3:SiO_2:NaF:H_2O$=(1:3:5:120). The raw material mixture was stirred uniformly, then sealed, heated 150° C. with stirring, and crystallized by rotation for 24 hours. The solid product was separated by centrifugation, washed with deionized water to neutrality, and dried in air at 100° C. to obtain a molecular sieve sample S17 to be used, named SiAl-GIS.

Example 18

Synthesis of CoAPO-GIS Molecular Sieve

A certain amount of aluminum isopropoxide, deionized water, phosphoric acid, cobalt acetate, dimethylamine ($C_2H_7N$) and 1,4-succinic acid ($C_4H_7NO_4$) were sequentially added to a 100 mL synthetic kettle. The molar ratio of the reactant was $CoAc.4H_2O:(iPrO)_3:H_3PO_4:C_2H_7N$:$C_4H_7NO_4:200H_2O$=(0.7:4:1:4:6:1.2:200). The raw material mixture was stirred uniformly, then sealed, heated 180° C. with stirring, and crystallized by rotation for 48 hours. The solid product was separated by centrifugation, washed with deionized water to neutrality, and dried in air at 100° C. to obtain a molecular sieve sample S18 to be used, named CoAPO-GIS.

Example 19

Synthesis of SAPO-GIS Molecular Sieve

Pseudoboehmite, deionized water, phosphoric acid, silica sol (30%), and propylamine were sequentially added to a synthesis kettle. The molar ratio of the reactant was $Al_2O_3$:$P_2O_5:SiO_2:4.0$ $PA:100H_2O$=(1:1:0.3:4:100). The raw material mixture was stirred uniformly, then sealed, heated 160° C. with stirring, and crystallized by rotation for 96 hours. The solid product was separated by centrifugation, washed with deionized water to neutrality, and dried in air at 100° C. to obtain a molecular sieve sample S19 to be used, named SAPO-GIS.

Example 20

Structure Characterization

Figure 2:
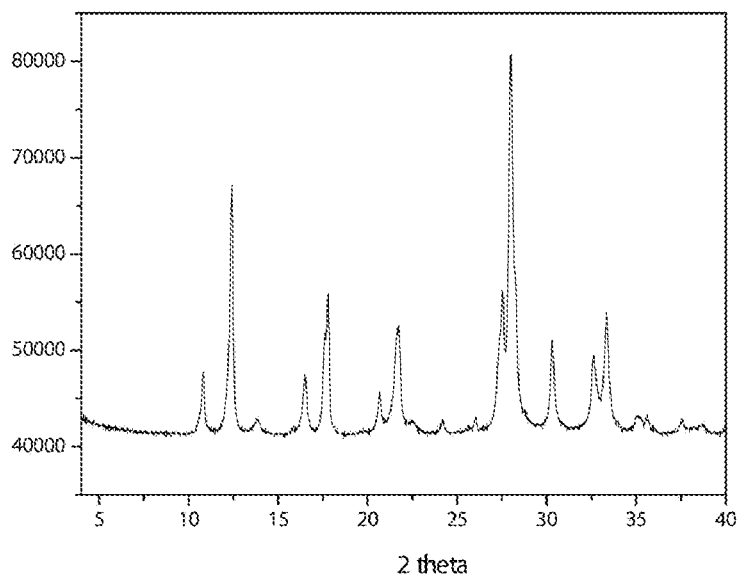
FIG. 2 is an XRD spectrum of the synthesized sample in Example 6.
Figure 3:
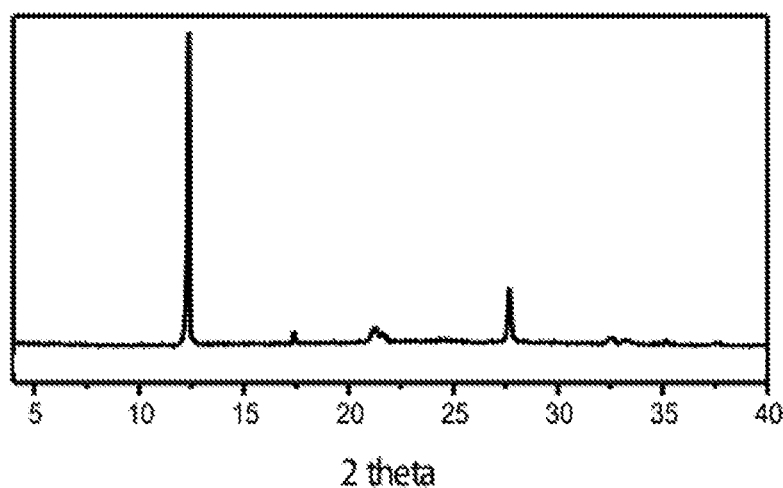
FIG. 3 is an XRD spectrum of the synthesized sample in Example 18.
Figure 4:
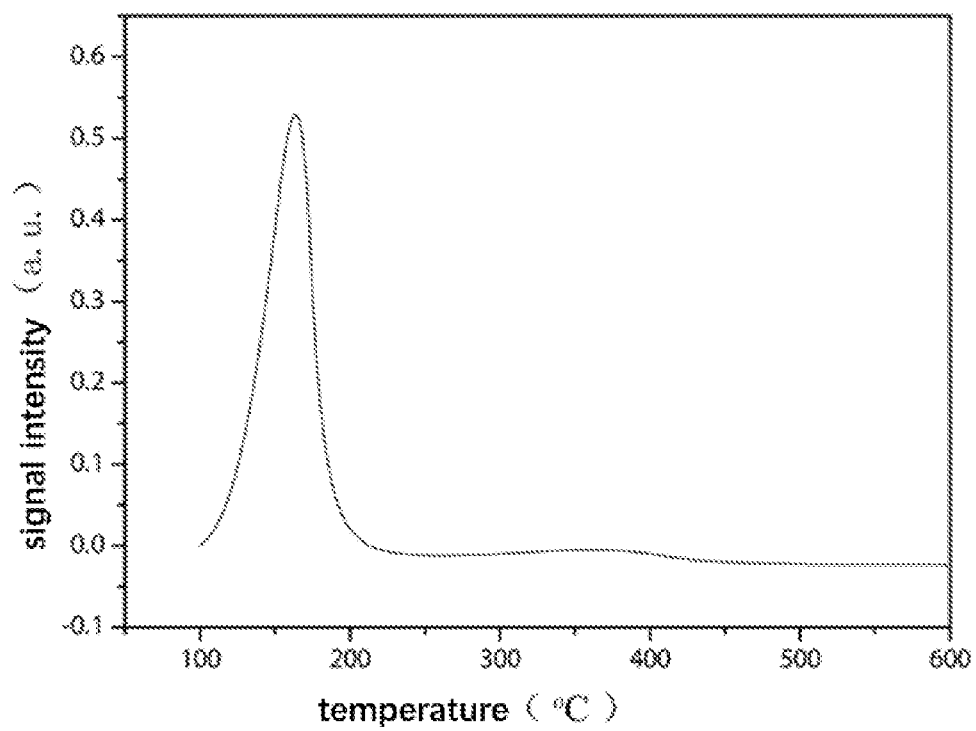
FIG. 4 is an NH$_3$-TPD curve of the SAPO-APD molecular sieve in an embodiment of the present application.

The samples prepared in Examples 1-19 were subjected to XRD characterization. The results showed that the synthesized samples were all pure phases, and there was no other heterogeneous molecular sieve. The XRD diffraction pattern of selected examples 2, 6 and 18 are shown in FIGS. 1-3 below. The XRD characterization data such as 2θ angle and the relative intensity are shown in Table 1. The sample in example 11 was characterized by $NH_3$-TPD. The results are shown in FIG. 4.

TABLE 1

| Example 1 | | Example 3 | | Example 5 | | Example 7 | |
|---|---|---|---|---|---|---|---|
| 2θ (°) | relative intensity | 2θ (°) | relative intensity | 2θ (°) | relative intensity | 2θ (°) | relative intensity |
| 9.05 | 100 | 11.92 | 20.5 | 10.96 | 50.3 | 10.95 | 40.1 |
| 11.55 | 73.76 | 11.98 | 72.2 | 12.7 | 100 | 12.05 | 45.2 |
| 11.6 | 33.44 | 15.50 | 30.5 | 16.8 | 48.3 | 12.35 | 100 |
| 13.15 | 80.0 | 15.58 | 25.1 | 18.1 | 70.2 | 12.7 | 20.1 |
| 13.2 | 20.69 | 20.01 | 100 | 21.1 | 12.3 | 14.0 | 15.1 |
| 13.65 | 56.73 | 21.42 | 28.2 | 22.2 | 20.1 | 14.15 | 30.1 |
| 14.3 | 12.81 | 23.4 | 76.0 | 24.7 | 18.3 | 15.5 | 21.4 |
| 14.35 | 12.96 | 26.02 | 95.1 | 26.4 | 11.5 | 17.2 | 15.6 |
| 16 | 16.61 | 26.7 | 65.1 | 27.8 | 82.2 | 17.4 | 33.1 |
| 18.2 | 25.41 | 26.87 | 28.9 | 28.7 | 92.1 | 18.65 | 21.8 |
| 19 | 15.99 | | | 30.6 | 20.5 | 27.9 | 50.1 |
| 20.95 | 16.83 | | | 33.4 | 15.6 | | |

| Example 9 | | Example 11 | | Example 13 | | Example 15 | |
|---|---|---|---|---|---|---|---|
| 2θ (°) | relative intensity | 2θ (°) | relative intensity | 2θ (°) | relative intensity | 2θ(°) | relative intensity |
| 13.4 | 100 | 12.9 | 100 | 21.6 | 50.6 | 13.6 | 90.2 |
| 15.01 | 74.24 | 18.5 | 19.8 | 24.68 | 100 | 16.4 | 35.8 |
| 16.49 | 73.76 | 20.61 | 20 | 24.83 | 63.1 | 16.5 | 46.9 |
| 19.12 | 33.44 | 20.71 | 90.0 | 25.89 | 20.8 | 18.5 | 53.7 |
| 19.3 | 80.0 | 21.4 | 16.8 | 26.3 | 22.8 | 24.8 | 100 |
| 20.3 | 20.69 | 25.1 | 10.2 | 26.8 | 50.1 | 25.0 | 86.7 |
| 21.5 | 56.73 | 28.8 | 18.7 | 29.5 | 11.0 | 26.3 | 15.9 |
| 25.4 | 12.81 | 29.4 | 19.5 | 30.8 | 28.1 | 28.9 | 15.0 |
| 25.5 | 12.96 | | | | | 30.5 | 35.5 |
| 27.8 | 16.61 | | | | | 32.4 | 84.4 |
| 28.08 | 25.41 | | | | | 32.7 | 91.2 |
| 31.32 | 15.99 | | | | | 34.6 | 50.6 |
| 33.6 | 100 | | | | | 39.4 | 35.2 |
| 29.8 | 20.13 | | | 38.6 | 18.1 | | |

Example 21

Evaluation of MTP Performance of SAPO Molecular Sieve

The SAPO molecular sieves synthesized in the above example are calcined in air at a temperature in a range of 400° C. to 800° C. for 2 hours to obtain the catalyst product to be used for evaluating MTP catalytic reaction. The catalytic performance evaluation operation is shown in the specific embodiment, and the process conditions used in study and catalytic results are shown in table 2. When referring to the calculation of the conversion rate in this example and in the following content, both methanol and dimethyl ether are regarded as reactants, and the selectivity corresponds to the value of the conversion rate at the highest point. As can be seen from table 2, the total selectivity to ethylene, propylene and C4 is close to 100% (the total selectivity may be equal to or slightly over 100% due to the detection error of the instrument).

TABLE 2

| Sample Number | Reaction temperature/ ° C. | Mass space velocity/ h$^{-1}$ | Conversion rate/ (wt %) | Selectivity (wt %) | | |
|---|---|---|---|---|---|---|
| | | | | ethylene | propylene | C4 |
| SAPO-AFN (S2) | 400 | 2 | 88.6 | 10.2 | 69.25 | 12.01 |
| SAPO-DFT (S4) | 375 | 2 | 75.8 | 9.48 | 72.88 | 18.10 |
| SAPO-SIV (S8) | 400 | 3 | 85 | 12.33 | 65.92 | 12.59 |
| SAPO-THO (S10) | 450 | 4 | 94 | 11.80 | 71.83 | 8.62 |
| SAPO-APD (S11) | 450 | 2 | 98.5 | 9.1 | 74.3 | 12.51 |
| SAPO-CAS (S13) | 350 | 1 | 80.5 | 8.74 | 61.79 | 20.21 |
| SAPO-EDI (S16) | 400 | 2 | 78.5 | 10.0 | 72.3 | 11.51 |
| SAPO-GIS (S19) | 400 | 2 | 85.8 | 6.48 | 72.88 | 10.10 |

Example 22

Evaluation of MTP Catalytic Performance of Silicon-Aluminum Molecular Sieve

The silicon-aluminum molecular sieve synthesized in the above embodiment was subjected to ion exchange to obtain a hydrogen-type molecular sieve. The specific process was as follows: the silicon-aluminum molecular sieve was calcined in air at a temperature in a range of 400° C. to 800° C. for 3 hours. Then, 100 g of ammonium nitrate was dissolved in 1300 ml of deionized water, and 20 g of calcinated molecular sieve sample was added in ammonium nitrate solution after ammonium nitrate was completely dissolved and stirred under an oil bath at 85° C. for 10 hours, stand for cooling, and then separated by centrifugation, and the sample was washed with deionized water to neutrality. The above ion exchange step was repeated for 2-4 times (twice for S6, four times for S12, and the others were exchanged for three times) to obtain an ammonium type molecular sieve sample. It was further calcined in air at a temperature in a range of 400° C. to 800° C. for 3 hours to obtain an MTP catalyst to be used. The catalytic performance evaluation operation is shown in the specific embodiment, and the process conditions used in study and catalytic results are shown in table 3.

TABLE 3

| Sample Number | Reaction temperature/ ° C. | Mass space velocity/ h$^{-1}$ | Conversion rate/ (wt %) | Selectivity (wt %) | | |
|---|---|---|---|---|---|---|
| | | | | ethylene | propylene | C4 |
| SiAl-PHI (S6) | 300 | 2 | 100 | 9.2 | 71.25 | 11.01 |
| SiAl-CAS (S12) | 300 | 2 | 99 | 8.18 | 72.88 | 10.10 |
| SiAl-EDI (S15) | 315 | 3 | 98 | 10.33 | 75.92 | 10.59 |
| SiAl-GIS (S17) | 350 | 2 | 95 | 6.48 | 72.08 | 13.10 |

Example 23

Evaluation of MTP Catalytic Performance of Transition Metal-Substituted Aluminophosphate Molecular Sieve The transition metal-substituted aluminophosphate molecular sieve synthesized in the above examples was calcinated carefully to remove the template agent to obtain an acidic molecular sieve. The molecular sieve sample was placed in a tube furnace, and then O$_2$ gas was introduced, and the temperature was raised to 400° C. at a heating rate of 1 degree/min and kept for 2 hours, and then raised to 500° C. at a heating rate of 0.5 degrees/min. The molecular sieve sample was calcinated at 500° C. for 4 hours to obtain MTP catalyst to be used. The catalytic performance operation is shown in the specific embodiment, and the process conditions used in study and catalytic results are shown in table 4.

TABLE 4

| Sample Number | Reaction temperature/ ° C. | Mass space velocity/ h$^{-1}$ | Conversion rate/ (wt %) | Selectivity (wt %) | | |
|---|---|---|---|---|---|---|
| | | | | ethylene | propylene | C4 |
| MnAlPO-AFN (S1) | 400 | 2 | 80.5 | 9.2 | 71.25 | 11.01 |
| CoAlPO-DFT (S3) | 400 | 2 | 89.1 | 9.18 | 72.88 | 10.10 |
| ZnAlPO-PHI (S5) | 415 | 1 | 92.5 | 11.33 | 75.92 | 10.59 |
| CoAlPO-SIV (S7) | 450 | 2 | 91.9 | 10.48 | 72.08 | 13.10 |
| ZnAlPO-THO (S9) | 400 | 2 | 93.7 | 9.18 | 72.88 | 10.10 |
| CoAlPO-EDI (S14) | 415 | 1 | 90.8 | 11.33 | 75.92 | 10.59 |
| CoAlPO-GIS (S18) | 450 | 2 | 91.2 | 10.48 | 72.08 | 13.10 |

Comparative Example 1

A comparative experiment of MTP catalytic performance was carried out by using the commonly used MTP catalysts SAPO-18 and ZSM-5. Both catalyst samples were calcined to remove the template agent for standby application. The molecular sieve sample was placed in a tube furnace, and then $O_2$ gas was introduced, and the temperature was raised to 400° C. at a heating rate of 1 degree/min and kept for 2 hours, and then raised to 500° C. at a heating rate of 0.5 degrees/min. The molecular sieve sample was calcinated at 500° C. for 4 hours to obtain MTP catalyst to be used. The catalytic performance operation is shown in the specific embodiment, and the process conditions used in study and catalytic results are shown in table 5.

TABLE 5[a]

| Sample Number | Reaction temperature/ °C. | Mass space velocity/ $h^{-1}$ | Conversion rate/ (wt %) | Selectivity (wt %) | | |
|---|---|---|---|---|---|---|
| | | | | ethylene | propylene | C4 |
| ZSM-5 | 400 | 2 | 100 | 13.63 | 34.59 | 11.01 |
| SAPO-18 | 400 | 2 | 99.8 | 24.18 | 44.58 | 20.10 |
| ZnAlPO-THO (S9) | 400 | 2 | 93.7 | 9.18 | 72.88 | 10.10 |

[a]ZDM-5 and SAPO-18 were selected with the best selectivity to low olefins for comparison.

As can be seen from the above examples, the molecular sieve catalyst of the present invention is capable of catalyzing the MTP reaction with high conversion rate and high selectivity, which is significantly superior to the catalysts of the prior art.

The above are only a few examples of the present application, and are not intended to limit the present application in any way. Although the present application is disclosed in the above with preferred example, it is not intended to limit the present application. Any one skilled in the art can understand that other changes and modifications by using the above technical content without departing from the scope of the technical solution of the present application are equivalent to equivalent embodiments and belong to the scope of the technical solution.

The above are only a few examples of the present application, and are not intended to limit the present application in any way. Although the present application is disclosed in the above with preferred example, it is not intended to limit the present application. Any one skilled in the art can understand that other changes and modifications by using the above technical content without departing from the scope of the technical solution of the present application are equivalent to equivalent embodiments and belong to the scope of the technical solution.

The invention claimed is:

1. A method for preparing propylene from methanol and/or dimethyl ether, comprising
bringing methanol and/or dimethyl ether into contact with a methanol to propylene catalyst to obtain propylene;
the methanol to propylene catalyst comprises a catalyst, wherein the catalyst comprises a molecular sieve with at least one-dimensional 8-membered ring channel in the molecular sieve structure, and the diameter of a sphere that can diffuse along the direction of the 8-membered ring channel is no less than 2.0 Å, the diameter of the sphere that can be included in the molecular sieve structure is no more than 6 Å.

2. The method of claim 1, wherein the molecular sieve is at least one selected from aluminosilicate molecular sieve, silicoaluminophosphate molecular sieve and transition metal-substituted aluminophosphate molecular sieve.

3. The method of claim 2, wherein a reaction temperature for bringing methanol and/or dimethyl ether into contact with the methanol to propylene catalyst is in a range of 300° C. to 500° C.

4. The method of claim 2, wherein a conversion rate of raw material is greater than 75% in the method.

5. The method of claim 2, wherein a single pass selectivity to propylene is greater than 60% in the method.

6. The method of claim 1, wherein the molecular sieve structure contains two-dimensional or three-dimensional 8-membered ring channels.

7. The method of claim 1, wherein the diameter of the sphere that can be included in the molecular sieve structure is in a range of 4.8 Å to 6 Å.

8. The method of claim 1, wherein a topology of the molecular sieve structure is at least one selected from AFN, DFT, PHI, SIV, THO, APD, CAS, EDI, GIS and VNI.

* * * * *